(12) United States Patent
Huang

(10) Patent No.: US 9,844,508 B2
(45) Date of Patent: Dec. 19, 2017

(54) TUMOR VACCINE AND METHOD FOR PRODUCING THE SAME

(71) Applicant: HUBEI SOUNDNY BIOTECHNOLOGY CO., LTD., Wuhan (CN)

(72) Inventor: Bo Huang, Wuhan (CN)

(73) Assignee: HUBEI SOUNDNY BIOTECHNOLOGY CO., LTD., Hubei (CN)

(*) Notice: Subject to any disclaimer, the term of this patent is extended or adjusted under 35 U.S.C. 154(b) by 0 days.

(21) Appl. No.: 14/557,393

(22) Filed: Dec. 1, 2014

(65) Prior Publication Data

US 2015/0086639 A1   Mar. 26, 2015

Related U.S. Application Data

(63) Continuation of application No. PCT/CN2013/076474, filed on May 30, 2013.

(30) Foreign Application Priority Data

May 31, 2012 (CN) .......................... 2012 1 0176820

(51) Int. Cl.
*A61K 9/00* (2006.01)
*A61K 9/14* (2006.01)
*A61K 39/00* (2006.01)
*A61K 9/51* (2006.01)

(52) U.S. Cl.
CPC ............ *A61K 9/009* (2013.01); *A61K 9/0019* (2013.01); *A61K 9/14* (2013.01); *A61K 9/5176* (2013.01); *A61K 39/0011* (2013.01); *A61K 2039/5152* (2013.01)

(58) Field of Classification Search
None
See application file for complete search history.

(56) References Cited

U.S. PATENT DOCUMENTS

| 7,625,573 B2* | 12/2009 | Zitvogel | A61K 38/1709 424/278.1 |
| 2005/0123596 A1* | 6/2005 | Kohane | A61K 9/1617 424/450 |
| 2007/0243159 A1* | 10/2007 | Selvaraj | A61K 39/0011 424/85.2 |

FOREIGN PATENT DOCUMENTS

| CN | 1265038 A | 8/2000 |
| CN | 1498658 A | 5/2004 |
| CN | 102302784 A | 1/2012 |
| WO | WO 99/03499 A1 | 1/1999 |
| WO | WO 99/58645 A1 | 11/1999 |

OTHER PUBLICATIONS

Dubensky et al., Sem. Immunol., 2010, 22(3)155-161.*
Kolowos et al., Scandinavian Journal of Immunology 2005, 61: 226-233.*
Max Schnurr et al., "Apoptotic Pancreatic Tumor Cells Are Superior to Cell Lysates in Promoting Cross-Priming of Cytotoxic T Cells and Activate NK and γδ T Cells" Cancer Research, vol. 62, No. 8, Apr. 15, 2002, pp. 2347-2352.
Aaron Tan et al., "The application of exosomes as a nanoscale cancer vaccine" International Journal of Nanomedicine, 2010; 5, pp. 889-900.
International Search Report of corresponding International PCT Application No. PCT/CN2013/076474, dated Sep. 12, 2013.
Chinese First Examination Report of corresponding China Application No. 201210176820.7, dated Jun. 23, 2014.

* cited by examiner

*Primary Examiner* — James D Schultz
(74) *Attorney, Agent, or Firm* — J.C. Patents

(57) ABSTRACT

The invention provides a tumor vaccine and method for producing the same. The tumor vaccine comprises cell vesicles derived from apoptotic tumor cells and an adjuvant. The invention further provides a preparation method of the tumor vaccine, comprising the steps of using the UV to irradiate the tumor cells to induce apoptosis, and collecting the cell vesicles released from the apoptotic tumor cells and then mixing the cell vesicles with the adjuvant to form the tumor vaccine. The tumor vaccine provided by the invention contains a broad and comprehensive tumor antigen spectrum, the defect that the existing tumor vaccine cannot have the killing capacity against the broad tumor cells can be overcome, and at the same time the tumor vaccine has good use safety and immune targeting property.

6 Claims, 6 Drawing Sheets

TUMOR VACCINE AND METHOD FOR PRODUCING THE SAME

CROSS-REFERENCE TO RELATED APPLICATIONS

This application is a continuation of International Application No. PCT/CN2013/076474, filed on May 30, 2013, which claims priority to Chinese Patent Application No. 201210176820.7, filed on May 31, 2012, both of which are hereby incorporated by reference in their entireties.

FIELD OF TECHNOLOGY

The present invention relates to a vaccine, and particularly to a tumor vaccine and a method for producing the same.

BACKGROUND

In recent years, tumor has become a type of disease severely endangering people's life, its treatment has become a subject to which numerous scientific researchers are dedicated. In addition to treatment methods such as chemotherapy, surgical resection, and the like that are commonly known to people, there has been a growing attention on tumor vaccine as a novel treatment method.

The tumor vaccine can achieve the purpose of eliminating or controlling the tumors mainly through activating patients' immune system, that is, utilizing tumor cells or tumor antigen to induce cell specific immuneresponse and humoral immune response of body, so as to enhance anti-cancer ability of the body and prevent growth, spread and recurrence of the tumors. The tumor vaccine can be divided into tumor cell vaccine, gene vaccine, polypeptide vaccine and others according to its source. The tumor cell vaccine is obtained from tumor tissues of the patients, and the inactivated tumor cells lose tumorigenicity but still keep immunogenicity, and then can be used to immunize the body; the immune mechanisms of gene vaccine mainly are through inserting tumor antigen genes into DNA expression vectors (generally are virus DNA), injecting the recombinant vectors into the bodies and expressing tumor antigen proteins to immunize the bodies; and the polypeptide vaccine are prepared through a chemical synthesis technology according to amino acid sequences of certain known or predicted antigen epitopes in the pathogenic antigen genes and then injected the polypeptide vaccine into the bodies for immunization.

However, most of the above vaccines have only entered clinical trials stage but not the clinical use stage. The main problems are as follows: the technology of transferring DNA into specific cells for expression is immature, and the safety problem of using exogenous DNA has not been solved; as the tumor cells show a high heterogeneity, that is, a plurality of tumor cells belong to the same type of tumors can express different antigens, thus T cells that activated by one tumor antigen (such as an antigen used by the polypeptide vaccine) can only kill part of the tumor cells, but not the tumor cells expressing other kinds of tumor antigens; and although the tumor cell vaccine can contain almost all kinds of the tumor antigens, the current study shows that tumor cell vaccine cannot effectively activate specific T cells and using tumor cell vaccine as vaccine is not ideal.

Therefore, how to provide a tumor vaccine which has no safety issues and can be effective to almost all the tumor antigens has becomes a problem to be solved urgently.

SUMMARY

The invention provides an application of cell vesicles in preparation of a tumor vaccine, and the cell vesicles derived from apoptotic tumor cells are used as antigens of the tumor vaccine, it is more conductive to solving the problems the existing tumor vaccine cannot effectively kill all kinds of the tumor antigens, and have poor targeting and safety issues.

The invention further provides a tumor vaccine. The cell vesicles derived from the apoptotic tumor cells are used as antigens and the obtained tumor vaccine contains a broad and comprehensive tumor antigen spectrum, and it is conductive for the tumor vaccine to improve their targeting effect and safety in clinical treatment.

The invention further provides a preparation method of a tumor vaccine, which achieves the preparation of the tumor vaccine by taking the cell vesicles derived from the apoptotic tumor cells as vaccine components.

The invention further provides a method for treating tumors or a method for preventing the generation of tumors. According to the method, all the tumor cells of individuals who suffer from cancer can be widespread killed, meanwhile the individuals who tend to suffer from tumor also can be immunized, and there are not any toxicity and side effects to the body.

In the application of the cell vesicles in the preparation of the tumor vaccine, the cell vesicles are derived from the apoptotic tumor cells.

As basic knowledge of the field, a cell is composed of a cell membrane and cellular content, while the cell membrane is composed of phospholipid bilayer and protein molecules embedded therein, whose spherical structure is maintained by the centripetal pulling force formed by the protein fibrils within the cell, which are called cytoskeleton. When a cell sensed to the stimulus of external signals (for example: ultraviolet rays) goes to apoptosis, some protein filament of the cytoskeleton attached to the cell membrane are broken, or lose adhesion, and their centripetal pulling force suddenly disappeared, such that the local cell membrane structure expands outward under the effect of the outgoing pulling force, and protrudes with cellular content wrapped therein, is released to the sub-hierarchical structure between the cell and molecules and cell vesicles are formed, whose size is mostly at nanoscale, that is the "cell vesicles" as described in this invention.

The main effect of the tumor vaccine in the body is to induce the proliferation and activation of tumor-specific T cells, and the basic process for achieve the above effect including the following steps: tumor antigens are taken up and processed by antigen-presenting cells (such as dendritic cells), and then tumor antigens is presented by the antigen-presenting cells to the tumor-specific T cells so as to activate and proliferate the T cells after its recognition of the tumor antigens, and when T cells arriving to the tumor site, specific killing against the tumor cells of the body. Wherein, the premise for completing the above process is the tumor antigens can be effectively taken up by antigen-presenting cells. As the antigen-presenting cells(such as dendritic cells) have strict requirements on volume and size when taking up foreign materials, and polypeptide molecules with very smaller volume and the whole tumor cell with very larger volume are difficult to be taken up by the antigen-presenting cells. Generally, the cell vesicles are 100-1000 nm and are very suitable for being taken up by the antigen-presenting cells (such as dendritic cells). Using such cell vesicles to prepare the tumor vaccine, after the tumor vaccine enters the body, the cell vesicles can be easily captured by the antigen-presenting cells, such that the tumor antigens can be effectively presented to the tumor-specific T cells and to activate these T cells. At the same time, the cell vesicles used by the invention contain almost all kinds of the tumor antigens of the tumor cells from which the cell vesicles are derived("all kinds of the tumor antigens" refer to the antigens of all of the tumor cells of one type of tumor), such that all the tumor cells of an individual suffering from cancer can be widespread killed, at the same time the individual tending to have the tumor can be immunized, and then the individual can have immunity to all of the tumor antigens, and the generation of tumors can be prevented.

According to the invention, the cell vesicles derived from the apoptotic tumor cells are adopted as the antigens of the tumor vaccine, the recommended cell vesicles are cell vesicles derived from the same type of tumor cells that need to be killed or prevented, and for example, these tumor cells can be a commercially available tumor cell lines. Compared with the tumor vaccine using an exogenous DNA vector or an amino acid sequence, the tumor vaccine using the cell vesicles can reduce the toxicity and the side effects on the body.

In the technical solution of the invention, the cell vesicles are obtained as follows: using the external conditions to stimulate the tumor cells (for example, using the UV to irradiate the tumor cells) to induce apoptosis, and collecting the cell vesicles released from the apoptotic tumor cells. Those of ordinary skills in this field can also select the appropriate methods for the apoptosis of the tumor cell according to different types of tumor that need to be treated. In order to conserve the tumor antigens in the cells, selecting the apoptosis method that can prevent chemical changes of the cells is advantageous. At the same time, the apoptosis of the tumor cells that being induced in the invention can be judged by standards known by those of ordinary skills in this field, for example, when the cancer cells observed become smaller and darker, confirming that these tumor cells have become apoptotic cells.

Further, the collection of the cell vesicles released from the apoptotic tumor cells can be performed with an ultracentrifuge under low-temperature conditions or a room-temperature conditions. Preferably, the cell vesicles can be collected at centrifugal force of 100 g~100000 g. The temperature during the collection is not particularly limited. As long as the degradation of the cell vesicles can be prevented, generally, the collection can be performed under the low-temperature conditions (about 4° C.).

In the technical solution of the invention, before using the UV to irradiate the tumor cells to induce apoptosis, it is also including culturing the tumor cells in a culture medium (such as a DMEM culture solution) containing substances required for the normally growth of the tumor cells.

Further, the particle size of the cell vesicles is 100-1000 nm.

Further, the tumor vaccine is used for ovarian cancer, melanoma, breast cancer, lung cancer, gastric cancer, colon cancer, liver cancer, bladder cancer, leukemia or glioma and other types of tumors.

The invention further provides a tumor vaccine, comprising cell vesicles derived from apoptotic tumor cells and an adjuvant.

Further, the adjuvant is an aluminum adjuvant.

Further, the preparation of the tumor vaccine including injection.

Further, the tumor cells including ovarian cancer cells, melanoma cells, breast cancer cells, lung cancer cells, gastric cancer cells, colon cancer cells, liver cancer cells, bladder cancer cells, leukemia cells or glioma cells.

In a specific implementation of the invention, the cell vesicles are obtained as follows: using the UV to irradiate the tumor cells to induce apoptosis, and collecting the cell vesicles released from the apoptotic tumor cells.

The invention further provides a preparation method of the tumor vaccine, comprising the processes of preparing the cell vesicles and preparing the tumor vaccine from the cell vesicles and the adjuvant.

Further, the preparation method of the tumor vaccine including the steps of using the UV to irradiate the tumor cells to induce apoptosis, and collecting the cell vesicles released by the apoptotic tumor cells and then mixing the cell vesicles with the adjuvant to form the tumor vaccine.

In the specific technical solution of the invention, preferably, the cell vesicles collected by the feasible methods are micro-particles with the particle size of 100-1000 nm basically. For example, the cell vesicles with the above particle size can be collected by controlling the centrifugal force, or can be collected with a filter membrane by controlling its pore diameter; and the temperature during the collection is not particularly limited, as long as the degradation of the cell vesicles can be prevented, generally, the collection can be carried out under the low-temperature condition (about 4° C.).

Further, the cell vesicles released from the apoptotic tumor cells can be collected, under the low-temperature or room-temperature condition, from the supernatant of the apoptotic tumor cells by using a centrifugal force of 100 g~100000 g. Further, the cell vesicles released from the apoptotic tumor cells can be collected by filtering the apoptotic tumor cells with a filter membrane of 0.1-3 nm.

Or the above cell vesicles can be collected by the combination of the filter membrane and the centrifuge, as long as the cell vesicles with the above particle size can be obtained.

Before using the UV to irradiate the tumor cells to induce apoptosis, the tumor cells can be pre-cultured (pre-incubated) in a culture medium (such as a DMEM culture medium) containing substances required for the normally growth of tumor cells.

The invention provides a method for treating tumors, including the process of administrating the tumor vaccine to patients with the tumor.

The invention provides a method to prevent the generation of tumors, including the process of administrating the tumor vaccine to individuals who tend to suffer from tumor.

The individuals tend to suffer from tumor in the invention refers to the individuals have genetic risk of suffering from the tumor or the individuals have other physical indicators that representing the risk of suffering from the tumor.

The tumor vaccine provided by the invention can adopt any preparations and medication specifications that are suitable for clinical applications, such as injection. The preparation method of the tumor vaccine further including the step of preparing the tumor vaccine into a required preparation according to a conventional vaccine preparation method, for example, preparing the tumor vaccine into injection. For example, the injection can be prepared as injection liquid by adding physiological saline, or can be prepared as injection powder, and the like. The usage amount of the adjuvant in the tumor vaccine provided by the invention is the conventional usage amount of the adjuvant in the tumor vaccine in the art.

Further, the administration dosage of the tumor vaccine provided by the invention can be appropriately determined according to the type of the tumor from which the cell vesicles are derived, and the stage of the tumor that the patients need to be treated or the age of the individuals tending to have the tumor and the like.

In the implementation of the invention, the immunization of a mouse with the tumor vaccine can be performed for three times, 0.03-0.08 ml of the tumor vaccine can be administrated to the mice each time, wherein each milliliter of tumor vaccine contains $4\times10^7$-$6\times10^7$ cell vesicles. Further, in addition to $4\times10^7$-$6\times10^7$ cell vesicles, each milliliter of tumor vaccine can further contain an appropriate amount of aluminum adjuvant, such as 0.04-0.06 mg. The mouse after being immunized with the tumor vaccine can significantly inhibit the generation of tumors.

The tumor vaccine provided by the invention can be administered by subcutaneous or intramuscular injection, so as to immunize individuals to inhibit the generation of tumors or kill the tumors.

The technical solution provided by the invention has the following advantages:

(1) For the tumor vaccine provided by the invention, the size of the cell vesicles can reach 100-1000 nm, which are very suitable for being taking up by the dendritic cells, and it is conductive to improve the efficiency of the antigen-presenting cells for presenting the antigens to the tumor-specific T cells, and enhancing the targeting killing ability of the tumor-specific T cells against the tumor cells.

(2) For the tumor vaccine provided by the invention, the cell vesicles contain abroad and comprehensive tumor antigen spectrum and can achieve effective killing against almost all of the tumor cells.

(3) The tumor vaccine provided by the invention can effectively kill a variety of tumor cells, and has small toxicity and side effects on the body, therefore it is safe to be used.

(4) The tumor vaccine provided by the invention can be used not only as a therapeutic vaccine, but also as a preventive vaccine, and can be used in different stages of treatment for tumors and for preventing the generation of tumors or effectively killing the existing tumor cells by activating an immune system of the body.

DETAILED DESCRIPTION

Figure 1A:
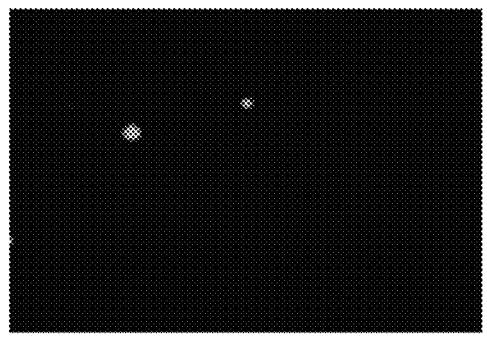
FIG. 1A shows a photo of cell vesicles produced from tumor cells without apoptosis treatment, FIG. 1B show s a photo of cell vesicles produced from the tumor cells after apoptosis treatment.

Term "cell vesicles" used in the invention refers to micro-particles that are generated after tumor cells apoptosis.

Tumor cells, medicaments and experimental animals used in the following embodiments:

*L. monocytogenes*, Murine hepatocarcinoma H22 (BALB/c mouse-derived), melanoma B16 (C57BL/6 mouse-derived), breast 4T1 (BALB/c mouse-derived) and colon MC26 (BALB/c mouse-derived) tumor cell lines, and mouse bone marrow cells were purchased from the ATCC company one of the United States or China Center for Type Culture Collection (CCTCC).

BALB/c mice and C57BL/6 mice (18 g weight) were purchased from the Laboratory Animal Center, College of Medicine of Wuhan University;

Carboxy fluoresceindiacetate succinimidyl ester (CFSE), PKH26, anti-mouse CD80, CD86 and MHC II antibodies were purchased from Sigma Company; cytokines GM-CSF and IL-4 were purchased from PeproTech Company; and a T cell separation kit was purchased from R&D Systems Company; an interferon gamma detection kit and a tumor cell killing detection kitwere purchased from Abcam Company.

Example 1: Cell Vesicles are Produced from Tumor Cells after a Treatment of Apoptosis 1. Experimental Materials and Reagents Murine hepatocarcinoma H22 tumor cells (hereafter called H22 cells), a fluorescent dye: carboxy fluoresceindiacetate succinimidyl ester (commercially available and green fluorescence), and an ultraviolet device 2. Experimental Procedures 1) H22 cells are cultured in a DMEM cell culture medium;

2) H22 cells ($2\times10^7$) are stained with the carboxy fluoresceindiacetate succinimidyl ester fluorescent dye, and cultured with fresh culture medium, then the stained H22 cells are divided into two groups (H22-1 group and H22-2 group), the cells of H22-1 group are exposed to ultraviolet irradiation for 60 min, the cells of H22-2 group are untreated 3) after the UV radiation, all the H22 cells in H22-1 group become significantly smaller and dimmer in 48 hours, confirming that these tumor cells are apoptosis, and the cell vesicles derived from the H22 cells are collected as follows: for example, the supernatants are centrifuged at 500 rpm, 1000 rpm, 5000 rpm, each for 10 minutes, then centrifuged for 1 minute at 14000 g to remove cells and debris, the obtained supernatant is further centrifuged for 60 min at 14000 g to pellet the cell vesicles, and used as an experiment group;

Another method for collecting the cell vesicles is filtering the above tumor cells with a filter membrane of 0.1-3 μm:

Step 1) the cell culture medium, which has been exposed to UV radiation for 60 min and confirmed the tumor cells in it have become apoptotic cells, is filtered with a filter element (3 μm pore size) so as to filter out the cells and the cell fragments above 3 μm and collect vesicle mixed solution (a);

Step 2) then the vesicle mixed solution (a) is separated by a tangential flow filter device with a pore size of Him, during this stage, an operable closed loop is formed by a liquid material tank filled with the vesicle mixed solution (a) and the tangential flow filter device, circulation-filtering of the vesicle mixed solution (a) is performed in this closed loop system and vesicle mixed solution (b) is drained out. In this closed loop, buffer solution is replenished into the liquid material tank, so as to prevent the failure of the filtration caused by high concentration of the vesicle mixed solution (a). After the filtration of this step, the vesicle mixed solution (b) below 1 μm is obtained;

Step 3) further, using a tangential flow filter device with a pore size of 0.1 μm to filter the vesicle mixed solution (b), during this stage, an operable closed loop is formed by the liquid material tank and the tangential flow filter device, circulation-filtering of the vesicle mixed solution (b) is performed in this closed loop system and waste liquid containing chemical preparations is discharged outside, vesicle mixed solution (c) is obtained. In this closed loop, the buffer solution is replenished into the liquid material tank, so as to prevent the failure of the filtration due to excessive concentration of the vesicle mixed solution (b);

Step 4) utilizing the tangential flow filter device to concentrate the vesicle mixed solution (c) to obtain the cell vesicles of the invention.

The cell vesicles derived from cells of the H22-2 group cultured under normal culture conditions are collected according to the same method above, as a control group. Although the group of the cells is not exposed to UV irradiation, a small quantity of cell vesicles can also be released due to normal cell death, thus the cell vesicles from cells of the H22-2 group can be collected as the control group.

3. Experimental Results

Figure 1B:
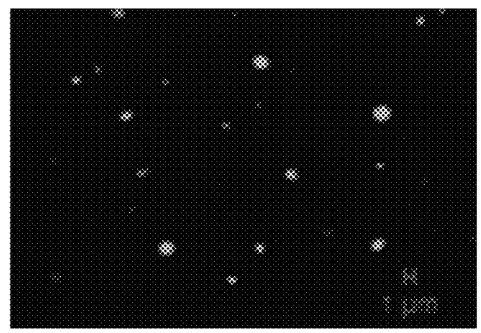

The cell vesicles from the experiment group and the cell vesicles from the control group are separately resuspended with 0.9% (g/ml)NS, and then observed under the two-photon fluorescence microscope after being smeared on a test sheet, respectively. It can be seen from FIG. 1 that, as a control group, there are fewer cell vesicles derived from the H22 cells that without being exposed to UV irradiation, and only a very few of green cell vesicles can be observed after smearing (see FIG. 1A), and as a experiment group, there are more cell vesicles derived from the H22 cells that exposed to UV irradiation, and a large number of green cell vesicles can be observed after smearing (see FIG. 1B), proving that the cell vesicles are released after the tumor cells being exposed to UV irradiation and the size of the cell vesicles is about 1 μm.

Changing the treatment method for inducing the apoptosis of the tumor cells, the same results can also be obtained.

Example 2: Cell Vesicles Produced from Tumor Cells can be Taken up by Dendritic Cells 1. Experimental Materials and Reagents Murine hepatocarcinoma H22 tumor cells(hereafter called H22 cells) and ultraviolet devices in this Example are the same as Example 1 and carboxy fluoresceindiacetate succinimidyl ester (CFSE) (green fluorescent dye) and PKH26 (red fluorescent dye) are commercially available.

2. Experimental Procedures

1) H22 cells are cultured as previously in Example 1, H22 cells ($1 \times 10^7$) are stain with carboxy fluoresceindiacetate succinimidyl ester and resuspended with fresh culture medium. Ultraviolet rays are used to irradiate the cell culture medium for 60 min, if smaller and dimmer H22 cells appear after being exposed to UV irradiation in 48 hours, cell vesicles with green fluorescence that produced from the apoptotic cancer cells which are stimulated by UV irradiation are collected according the method in example 1;

2) Mouse bone marrow cells are collected and cultured in the culture medium, and cytokines GM-CSF and IL-4 are added to the cell culture medium when $10^6$/ml Mouse bone marrow cells are in medium. After cultured for 6 days, the bone marrow cells are induced into dendritic cells, followed by staining with red fluorescent dye PKH26.

3) Cell vesicles with green fluorescence produced previously and the dendritic cells with red fluorescence are incubated under the condition of 37° C.

3. Experimental Results

Figure 2:
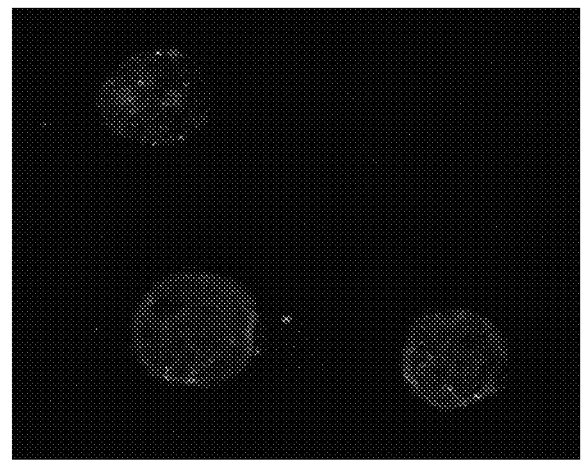
FIG. 2 shows that the cell vesicles can be taken up by dendritic cells.

After 4 hours incubation of the cell vesicles with green fluorescent and the dendritic cells with red fluorescent, the dendritic cells are washed three times, then observed under the fluorescent microscope after smeared. Cell vesicles (green fluorescent) can be taken up by the dendritic cells (red fluorescent) (FIG. 2).

Example 3: after Dendritic Cells Taking Up Cell Vesicles, the Expression of Co-Stimulatory Signal Molecules are Up-Regulated 1. Experimental Materials and Reagents Murine hepatocarcinoma H22 cells used by this Example are the same in Example 1, dendritic cells are the same in Example 2, and fluorescence-labeled anti-mouse CD80, anti-mouse CD86 and anti-mouse MHC II antibodies are commercially available.

2. Experimental Procedures 1) the method for culturing dendritic cells is the same in Example 2; and the cell vesicles of the H22 cells are prepared by the method of Example 1, and the method for the dendritic cells to take up the H22 cells is the same in Example 2.

2) the dendritic cells are co-incubated with cell vesicles for 48 h, and the dendritic cells taking up the cell vesicles are used as an experiment group; and the dendritic cells incubated alone for 48 h are used as a control group.

3) the dendritic cells in both groups are collected and stained with the antibodies: anti-mouse CD80, anti-mouse CD86 and anti-mouse MHC II.

3. Experimental Results

Figure 3:
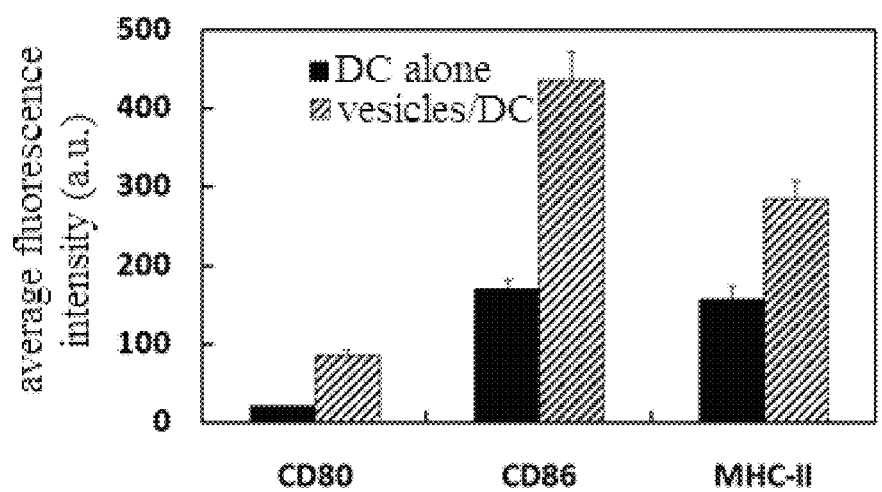
FIG. 3 shows that after the dendritic cells taking up the cell vesicles, the expression of co-stimulatory signal molecules is up-regulated.

The results show that, compared with the co-stimulatory signal molecules such as CD80, CD86 and MHC II type molecules in the dendritic cells of the control group (the dendritic cells without taking up the tumor cell vesicles, namely DC alone), these co-stimulatory signal molecules in the dendritic cells taking up the tumor cell vesicles (namely vesicles/DC) are significantly upregulated, (see FIG. 3), proving that the cell vesicles can effectively induce the maturation of the dendritic cells and up-regulate the expression of the co-stimulatory signal molecules.

Example 4: Proliferation and Activation of Tumor-Specific T Cells can be Induced by the Dendritic Cells Taking Up Cell Vesicles 1. Experimental Materials and Reagents Murine hepatocarcinoma H22 are the same in Example 1; mouse bone marrow cells are the same in Example 2; and a T cell separation kit, an interferon gamma detection kit for detecting the activation performance of T cells, BALB/c mice and *L. monocytogenes* are commercially available.

2. Experimental Procedures

1) Using the method of Example 1 to obtain cell vesicles from the apoptotic H22 mouse liver cancer cells; and using the method of Example 2 to obtain dendritic cells;

2) the H22 mouse liver cancer cells are cultured in a DMEM culture medium, $3\times10^5$ H22 mouse liver cancer cells are subcutaneously inoculating to 6 BALB/c mice, after 15 days mouse spleens are taken from these 6 BALB/c mice, T cells (containing liver cancer-specific T cells, and hereinafter referred to as tumor-specific T cells) are separated from the spleens of the BALB/c mice by the T cell separation kit;

2000 *L. monocytogenes* are intravenously injecting to the 6 BALB/c mice, after 7 days mouse spleens are taken from these 6 BALB/c mice, and the T cells (containing Listeria-specific T cells, and hereinafter referred to as Listeria-specific T cells) are separated from the spleens of the BALB/c mice by T cell separation kit.

3) the cell vesicles of the H22 mouse liver cancer cells obtained in step 1) and the dendritic cells are incubated for 48 h and the dendritic cells taking up the cell vesicles are obtained, and used as a experiment group; and at the same time the dendritic cells alone are incubated for 48 h, and used as a control group.

4) the dendritic cells in the experiment group are divided into two equal parts, and one part of the dendritic cells is co-cultured with Listeria-specific T cells for 72 h with a ratio of 1:10, the other part of the dendritic cells is co-cultured with tumor-specific T cells for 72 h with a ratio of 1:10, and then the proliferation of the above T cells is detected by tritium-labeled thymidine method; and the level of interferon gamma in the supernatant of the culture medium is detected by utilizing the interferon gamma detection kit;

At the same time the dendritic cells in the control group are divided into two equal parts, and one part of the dendritic cells is co-cultured with Listeria-specific T cells for 72 h with a ratio of 1:10, the other part of the dendritic cells is co-cultured with tumor-specific T cells for 72 h with a ratio of 1:10, and then the proliferation of the above T cells is detected by tritium-labeled thymidine method; and the level of interferon gamma in the supernatant of culture medium is detected by utilizing the interferon gamma detection kit.

3. Experimental Results

Figure 4A:
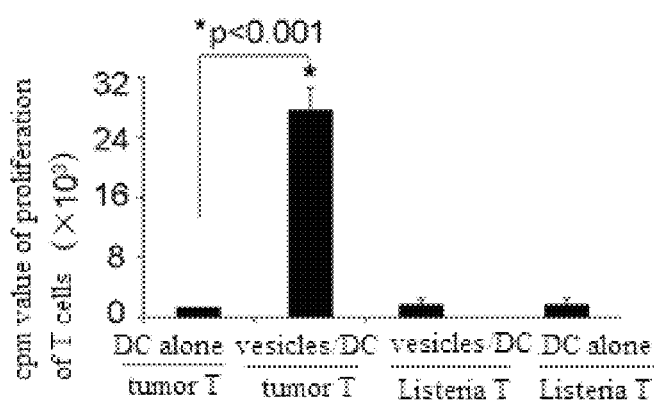
FIG. 4A and FIG. 4B show that after the dendritic cells taking up the cell vesicles, tumor-specific T cells are induced to activate and proliferate.
Figure 4B:
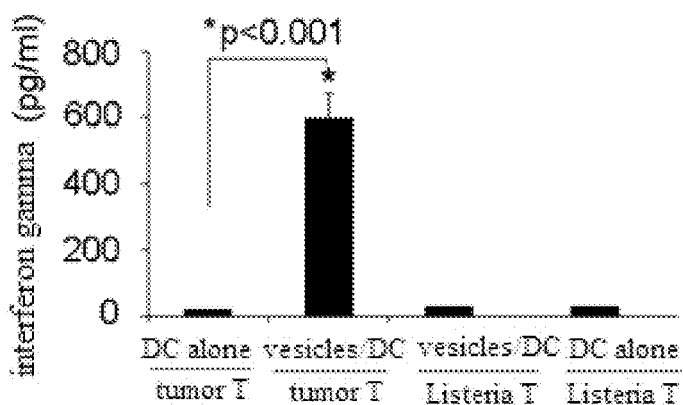

As shown in FIG. 4A, the dendritic cells without taking up the cell vesicles (namely DC alone) have a very small proliferation effect to the tumor-specific T cells (namely tumor T), the dendritic cells taking up the cell vesicles (namely vesicles/DC) can effectively induce the proliferation of the tumor-specific T cells, which shows a significant difference between the two groups,  indicates P<0.001, student' t test was used, it shows that the effect of the dendritic cells taking up the cell vesicles on inducing the proliferation of the tumor-specific T cells is significantly higher than that of the dendritic cells without taking up the cell vesicles, and the two kinds of dendritic cells have almost no effect on the proliferation of the Listeria-specific T cells (namely Listeria T); FIG. 4B shows that, the dendritic cells without taking up the cell vesicles have a very small effect on inducing the tumor-specific T cells to produce the interferon gamma; the dendritic cells taking up the cell vesicles can effectively induce the tumor-specific T cells to produce the interferon gamma, which shows a significant difference between the two groups. indicates P<0.001, student' test was used, it shows that the effect of the dendritic cells taking up the cell vesicles on inducing the tumor-specific T cells to produce the interferon gamma is significantly higher than that of the dendritic cells without taking up the cell vesicles, and the two kinds of dendritic cells have almost no effect on inducing the Listeria-specific T cells to produce the interferon gamma.

Example 5: Tumor Cells are Killed by Activated Tumor-Specific T Cells

1. Experimental Materials and Reagents

Cell vesicles were derived from H22 mouse liver cancer cells (hereafter called H22 cells), dendritic cells and tumor-specific T cells used by this Example are the same as those in Example 4; a kit for detecting the killing ability of the T cells against tumor cells, and BALB/c mice are commercially available.

2. Experimental Procedures 1) the H22 cells are cultured in a DMEM culture medium, $3\times10^5$ H22 cells are subcutaneously inoculated to 6 BALB/c mice, after 15 days mouse spleens are taken from these 6 BALB/c mice, and T cells (containing liver cancer-specific T cells therein) are separated from the spleens by the T cell separation kit, that is, tumor-specific T cells are obtained.

2) the cell vesicles of derived from the H22 cells are incubated with dendritic cells for 48 h, and dendritic cells taking up the cell vesicles are obtained, and used as an experiment group; and at the same time the dendritic cells are cultured alone for 48 h, and used as a control group.

3) the tumor-specific T cells are divided into two equal parts, and one part of the tumor-specific T cells is co-cultured with the dendritic cells of the experiment group for 7 days with a ratio of 10:1, the other part of the tumor-specific T cells is co-cultured with the dendritic cells of the control group for 7 days with a ratio of 10:1, the tumor-specific T cells being separately induced by the dendritic cells of the experiment group and control group are collected, and the induced tumor-specific T cells also can be called as effector cells, including effector cells of the experiment group and effector cells of the control group.

4) CFSE-labeled H22 cells are used as target cells, dividing the target cells into two equal groups, and one part of the target cells is co-cultured with the effector cells of the experiment group for 4 hours with a ratio of 1:5, 1:25, 1:50, the other part of the target cells is co-cultured with the effector cells of the control group for 4 hours with a ratio of 1:5, 1:25, 1:50, the T cells are collected after 4 hours, and the killing ability of the T cells against the tumor cells is detected as follows: tumor cells were stained with PE-labeled Annexin V for detecting the killing ability of the T cells against tumor cells, the killing rate against the tumor cells is analyzed by flow cytometry;

3. Experimental Results

Figure 5:
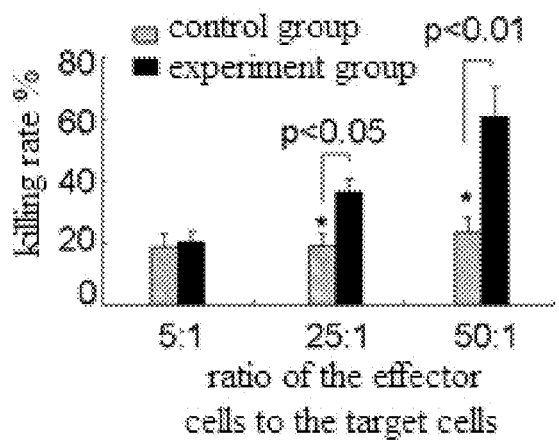
FIG. 5 shows that tumor cells are killed by the activated tumor-specific T cells.

It can be seen from FIG. 5 that, when the ratio of the target cells to the effector cells is 1:5, these is no significant difference between the killing rates of effector cells of the experiment group and effector cells of the control group; when the ratio of the target cells to the effector cells is 1:25, the p value between the killing rates of the effector cells of the experiment group and the control group experiment is less than 0.05, which shows a significant difference, that is, compared with the effector cells of the control group, the effector cells of the experiment group have the significantly improved killing ability against the tumor cells; when the ratio of the target cells to the effector cells is 1:50, the p value between the killing rates of the experiment group and the control group experiment is less than 0.01, which shows a more significant difference, that is, compared with the effector cells of the control group, the effector cells of the experiment group have more significantly improved killing ability against the tumor cells.

Example 6: Mice are Immunized by Tumor Cell Vesicles, and Strong Immune Reactions of the Mice are Induced 1. Experimental Materials and Reagents Murine hepatocarcinoma H22 tumor cells (hereafter called H22 cells) used in this Example are the same as those in Example 1, and BALB/c mice (18 g weight) are purchased from Centre of Medical Experimental Animals of Hubei Province (Wuhan, China).

2. Experimental Procedures 1) the cell vesicles of the H22 cells obtained are same as described in Example 1;

2) 10 BALB/c mice are divided into two equal groups:

One group of the BALB/c mice is used as an experiment group, and the BALB/c mice are subcutaneous immunized with the cell vesicles obtained above, the specific process of the subcutaneous immunization is as follows: the first immunization is performed on the first day (administration of 0.05 ml of physiological saline containing $5 \times 10^7$ cell vesicles to the BALB/c mice), the second immunization is performed on the second day (administration of 0.05 ml of NS containing $5 \times 10^7$ cell vesicles to the BALB/c mice), the third immunization is performed on the seventh day (administration of 0.05 ml of NS containing $5 \times 10^7$ cell vesicles to the BALB/c mice), mice were scarified and popliteal fossa lymph nodes isolated on the eighth day;

the other group of BALB/c mice is used as a control group, and the BALB/c mice had been given a placebo (i.e. physiological saline), and the specific process for giving the placebo is as follows: the first administration of the placebo is performed on the first day (0.05 ml of NS is administrated to the BALB/c mice), the second administration of the placebo is performed on the second day (0.05 ml of NS is administrated to the BALB/c mice), the third administration of the placebo is performed on the seventh day (0.05 ml of NS is administrated to the BALB/c mice), mice were scarified and popliteal fossa lymph nodes of the mice were isolated on the eighth day.

3. Experimental Results

Figure 6:
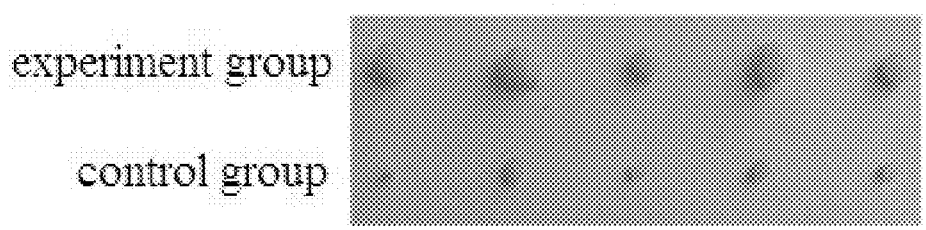
FIG. 6 shows that strong immune reactions of mice are induced by immunization the mice with the tumor cell vesicles.

It can be seen from FIG. 6, compared with the mice in the control group, the popliteal fossa lymph nodes of the mice in the experiment group subcutaneous immunized with the cell vesicles are much larger than control group, indicating strong immune reactions of mice can be induced by immunization the mice with the tumor cell vesicles.

Example 7: The Growth of Tumors can be Inhibited and the Survival Time of Tumor-Bearing Mice can be Prolonged by Immunization the Mice with the Tumor Cell Vesicles 1. Experimental Materials and Reagents Murine hepatocarcinoma H22 tumor cells (hereafter called H22 cells) used in this Example are the same as those in Example 1, BALB/c mice (18 g weight) for experiments are purchased from Centre of Medical Experimental Animals of Hubei Province (Wuhan, China).

2. Experimental Procedures 1) cell vesicles of the H22 cells obtained are same as described in Example 1;

2) 12 BALB/c mice are divided into two equal groups:

One group of the BALB/c mice is used as an experiment group and the BALB/c mice are subcutaneous immunized on the right costal margin with the cell vesicles obtained above, the specific process of the subcutaneous immunization is as follows: the first immunization is performed on the first day (administration of 0.05 ml of NS containing $5 \times 10^7$ cell vesicles to the BALB/c mice), the second immunization is performed on the second day (administration of 0.05 ml of NS containing $5 \times 10^7$ cell vesicles to the BALB/c mice), the third immunization is performed on the seventh day (administration of 0.05 ml of NS containing $5 \times 10^7$ cell vesicles to the BALB/c mice), the BALB/c mice are subcutaneous inoculated on the left costal margin with $3 \times 10^5$ H22 cells on the eighth day, and the generation of tumors and the survival time of the mice are observed;

The other group of BALB/c mice is used as a control group and the BALB/c mice had been given a placebo (i.e. NS), and the specific process for giving the placebo is as follows: the first administration of the placebo is performed on the first day (0.05 ml of NS is administrated to the BALB/c mice), the second administration of the placebo is performed on the second day (0.05 ml of NS is administrated to the BALB/c mice), the third administration of the placebo is performed on the seventh day (0.05 ml of NS is administrated to the BALB/c mice), the BALB/c mice are subcutaneous inoculated on the left costal margin with $3 \times 10^5$ H22 cells on the eighth day, and the generation of tumors and the survival time of the mice are observed.

3. Experimental Results

Figure 7A:
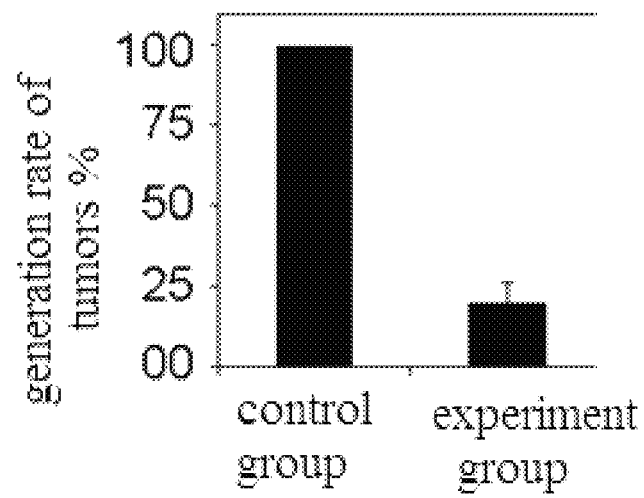
FIG. 7A and FIG. 7B show that the growth of tumor can be inhibited and the survival times of the tumor-bearing mice can be prolonged by immunization the tumor-bearing mice with the tumor cell vesicles.
Figure 7B:
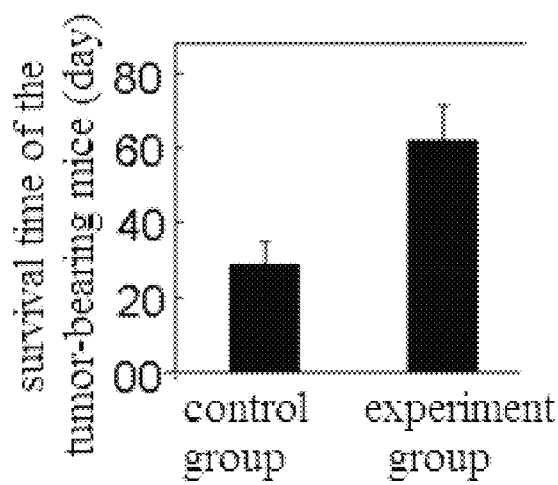

It can be seen from FIG. 7A and FIG. 7B, compared with the mice in the control group being given the placebo, the mice in the experiment group being immunized with the cell vesicles can effectively inhibit the generation of tumors(80% of mice were tumor free) and significantly prolong the survival time of the tumor-bearing mice.

Example 8: Immunization of Mice with Cell Vesicles has No Side Effect on Liver and Kidney Functions 1. Experimental Materials and Reagents Murine hepatocarcinoma H22 tumor cells (hereafter called H22 cells) used by this Example are the same as those in Example 1, BALB/c mice (18 g weight) for experiments are purchased from Centre of Medical Experimental Animals of Hubei Province (Wuhan, China).

2. Experimental Procedures 1) cell vesicles of the H22 cells are obtained through the method same as described in Example 1;

2) 16 BALB/c mice are divided into two equal groups:

One group of the BALB/c mice is used as an experiment group and the BALB/c mice are subcutaneous immunized on the right costal margin with the cell vesicles obtained above, the specific process of the subcutaneous immunization is as follows: the first immunization is performed on the first day (administration of 0.05 ml of NS containing $5 \times 10^7$ cell vesicles to the BALB/c mice), the second immunization is performed on the second day (administration of 0.05 ml of NS containing $5 \times 10^7$ cell vesicles to the BALB/c mice), the third immunization is performed on the seventh day (administration of 0.05 ml of NS containing $5 \times 10^7$ cell vesicles to the BALB/c mice), and then the BALB/c mice are fed normally every day;

The other group of BALB/c mice is used as a control group and the BALB/c mice had been given a placebo (i.e. NS), and the specific process for giving the placebo is as follows: the first administration of the placebo is performed on the first day (0.05 ml of NS is administrated to the BALB/c mice), the second administration of the placebo is performed on the second day (0.05 ml of NS is administrated to the BALB/c mice), the third administration of the placebo is performed on the seventh day (0.05 ml of NS is administrated to the BALB/c mice), and then the BALB/c mice are fed normally every day.

3) tail veinblood is collected from the BALB/c mice on the eighth day, and the content of glutamic-pyruvic transaminase and creatinine in the blood is detected.

3. Experimental Results

Figure 8A:
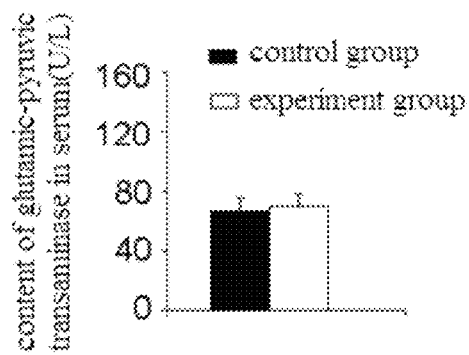
FIG. 8A and FIG. 8B show that the cell vesicles have no influence on liver and kidney functions.
Figure 8B:
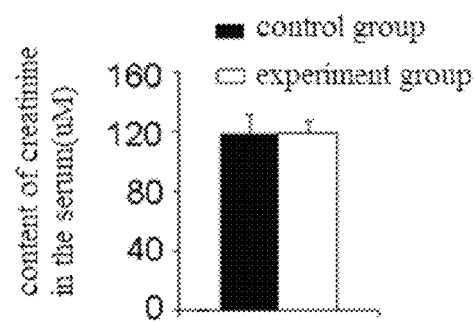

It can be seen from FIG. 8A and FIG. 8B that compared with the content of glutamic-pyruvic transaminase and creatinine in the serum of the control group mice being given the placebo, the content of glutamic-pyruvic transaminase and creatinine in the serum of the experiment group mice being immunized with the cell vesicles does not substantially changed, indicating that the immunization of the BALB/c mice with the cell vesicles has no substantially side effect on the liver and kidney functions.

Example 9: Anti-Tumor Effect of Tumor Vaccine

1. Experimental Materials and Reagents

BALB/c mice (18 g weight) for experiments are purchased from Centre of Medical Experimental Animals of Hubei Province (Wuhan, China).

2. Experimental Procedures 1) cell vesicles of the H22 cells are obtained through the method same as described in Example 1;

2) 20 BALB/c mice are divided into two equal groups: the BALB/c mice in one group are subcutaneous immunized on the right costal margin with the cell vesicles obtained above, the specific process of the subcutaneous immunization is as follows: the first immunization is performed on the first day (administration of 0.05 ml of NS containing $5 \times 10^7$ cell vesicles to the BALB/c mice), the second immunization is performed on the second day (administration of 0.05 ml of NS containing $5 \times 10^7$ cell vesicles to the BALB/c mice), the third immunization is performed on the seventh day (administration of 0.05 ml of NS containing $5 \times 10^7$ cell vesicles to the BALB/c mice), the BALB/c mice are subcutaneous inoculated on the left costal margin with $1 \times 10^6$ H22 cells on the eighth day, and the generation of tumors is observed; the BALB/c mice in the other group are subcutaneous immunized on the right costal margin with a mixture of the vesicles obtained above and an adjuvant (e.g. aluminum adjuvant), and the specific process of the subcutaneous immunization is as follows: the first immunization is performed on the first day (administration of 0.05 ml of NS containing $5 \times 10^7$ cell vesicles and 0.05 mg aluminum adjuvant to the BALB/c mice), the second immunization is performed on the second day (administration of 0.05 ml of NS containing $5 \times 10^7$ cell vesicles and 0.05 mg aluminum adjuvant to the BALB/c mice), the third immunization is performed on the seventh day (administration of 0.05 ml of NS containing $5 \times 10^7$ cell vesicles and 0.05 mg aluminum adjuvant to the BALB/c mice), the BALB/c mice are subcutaneous inoculated on the left costal margin with $1 \times 10^6$ H22 cells on the eighth day, and the subcutaneous tumor volume of the mice are observed;

3. Experimental Results

Figure 9:
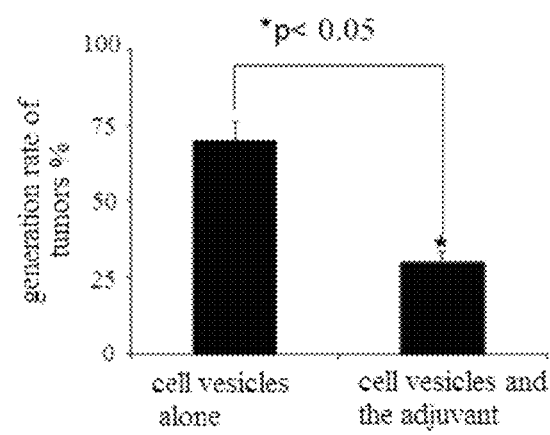
FIG. 9. An anti-tumor effect of the tumor vaccine.

It can be seen from FIG. 9, administrating the tumor vaccine containing the cell vesicles, at least 30% of the mice are tumor free; but administrating the tumor vaccine containing both the cell vesicles and the adjuvant, 70% of mice are tumor free, and the P value between the two is less than 0.05, indicating that, compared with the administration of the tumor vaccine containing the cell vesicles alone, administration of the tumor vaccine containing both the cell vesicles and the adjuvant can achieve a better anti-tumor immunity.

Example 10 in Addition to Liver Cancer, the Technical Solution of the Invention is Also Effective for Other Types of Tumor 1. Experimental Materials and Reagents Different tumor cell lines including a B16 mouse melanoma cell line (C57BL/6 genetic background), a 4T1 mouse breast cancer cell line (BALB/c genetic background) and a MC26 mouse colon cancer cell line (BALB/c genetic background); and C57 mice and BALB/c mice for experiments are purchased from Centre of Medical Experimental Animals of Hubei Province (Wuhan, China), each weighing about 18 grams.

2. Experimental Procedures 1) the above tumor cell lines are respectively cultured in a DMEM culture medium, $1 \times 10^8$ cells were irradiated by ultraviolet for 60 min, confirming that these tumor cells have become apoptotic cells after being induced by UV, if the cells of each tumor cell line become significantly smaller and darker within 48 h after being exposed to UV irradiation, collecting the cell vesicles produced from the apoptotic tumor cells of each tumor cell line according to the methods described in Example 1.

2) the cell vesicles from each tumor cell line are separately mixed with the adjuvant (such as the aluminum adjuvant) and physiological saline, such that tumor vaccines for each kind of tumors are produced.

3) the anti-tumor effects of the each tumor vaccine against the mice bearing the same tumors are detected, the detection method is illustrated below by taking the tumor vaccine of mouse breast cancer (wherein, each milliliter of the tumor vaccine of mouse breast cancer contains $5 \times 10^7$ cell vesicles derived from 4T1 mouse breast cancer cells and 0.05 mg of aluminum adjuvant) as an example:

16 normally BALB/c mice are divided into two equal groups, the BALB/c mice in one group are subcutaneous immunized on the right costal margin with the tumor vaccine of mouse breast cancer obtained above, the specific process of the subcutaneous immunization is as follows: the first immunization is performed on the first day (administration of 0.05 ml of the tumor vaccine of mouse breast cancer to the BALB/c mice), the second immunization is performed on the second day (administration of 0.05 ml of the tumor vaccine of mouse breast cancer to the BALB/c mice), the third immunization is performed on the seventh day (administration of 0.05 ml of the tumor vaccine of mouse breast cancer to the BALB/c mice), the BALB/c mice are subcutaneous inoculated on the left costal margin with $3 \times 10^5$ 4T1 mouse breast cancer cells on the eighth day, and the generation of tumors is observed; the BALB/c mice in other group had been given a placebo(i.e. NS), and the specific process for giving the placebo is as follows: the first administration of the placebo is performed on the first day (0.05 ml of NS is administrated to the BALB/c mice), the second administration of the placebo is performed on the second day (0.05 ml of NS is administrated to the BALB/c mice), the third administration of the placebo is performed on the seventh day (0.05 ml of NS is administrated to the BALB/c mice), the BALB/c mice are subcutaneous inoculated on the left costal margin with $3 \times 10^5$ 4T1 mouse breast cancer cells on the eighth day, and the subcutaneous tumor nodules of the mice are observed.

3. Experimental Results

Figure 10:
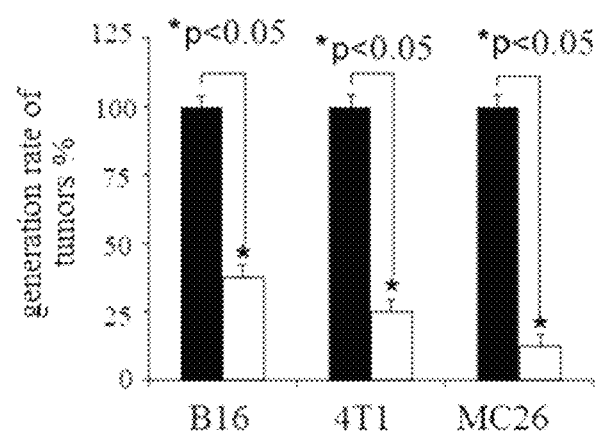
FIG. 10. Immunizing the mice bearing different tumors with the tumor cell vesicles, the growth of the tumors can be inhibited.

As shown in FIG. 10, for the tumor cells of the B16 mouse melanoma cell line (C57BL/6 genetic background), the 4T1mouse breast cancer cell line (BALB/c genetic background) and the MC26mouse colon cancer cell line (BALB/c genetic background), compared with the mice in the control groups being given a placebo(black filled part in FIG. 10), the mice in the experiment groups being immunized with the corresponding tumor vaccine can significantly inhibit the generation of tumors, the p value between each experiment group and the corresponding control group is less than 0.05, and about 80% of mice are tumor free, which means generation of tumors can be prevented.

What is claimed is:

1. A tumor vaccine, comprising microparticles, wherein the microparticles are cell vesicles derived from apoptotic tumor cells, and an adjuvant, wherein the microparticles are generated by cellular membrane encapsulating cytosolic contents, and wherein the particle size of the microparticles is 100-1000 nm;
   wherein the microparticles are obtained by: centrifuging cell culture medium that contains apoptotic tumor cells and collecting a first supernatant; centrifuging the first supernatant at a centrifugal force of not more than 14000 g so as to remove cells and debris, and collecting a second supernatant; further centrifuging the second supernatant at a centrifugal force of 14,000 g-100,000 g to obtain the microparticles.

2. The tumor vaccine according to claim 1, wherein the adjuvant is an aluminum adjuvant.

3. The tumor vaccine according to claim 1, wherein the vaccine is prepared for injection.

4. The tumor vaccine according to claim 1, wherein the tumor cells comprise ovarian cancer cells, melanoma cells, breast cancer cells, lung cancer cells, gastric cancer cells, colon cancer cells, liver cancer cells, bladder cancer cells, leukemia cells or glioma cells.

5. The tumor vaccine according to claim 1, wherein the cell vesicles are obtained as follows: using the UV to irradiate the tumor cells to induce apoptosis, and collecting the cell vesicles released from the apoptotic tumor cells.

6. The tumor vaccine according to claim 1, wherein the vaccine is prepared for injection, and one milliliter of the vaccine contains $4\times10^7$-$6\times10^7$ cell vesicles and 0.04-0.06 mg adjuvant.

* * * * *